US010695163B2

(12) United States Patent
Inoue

(10) Patent No.: US 10,695,163 B2
(45) Date of Patent: Jun. 30, 2020

(54) STENT-GRAFT

(71) Applicant: PTMC Institute, Kyoto-shi, Kyoto (JP)

(72) Inventor: Kanji Inoue, Kyoto (JP)

(73) Assignee: PTMC INSTITUTE, Kyoto-Shi, Kyoto (JP)

(*) Notice: Subject to any disclaimer, the term of this patent is extended or adjusted under 35 U.S.C. 154(b) by 0 days.

(21) Appl. No.: 14/975,396

(22) Filed: Dec. 18, 2015

(65) Prior Publication Data

US 2017/0007391 A1 Jan. 12, 2017

(30) Foreign Application Priority Data

Jul. 10, 2015 (JP) ................. 2015-138551

(51) Int. Cl.
*A61F 2/07* (2013.01)
*A61F 2/89* (2013.01)
*A61F 2/06* (2013.01)

(52) U.S. Cl.
CPC .................. *A61F 2/07* (2013.01); *A61F 2/89* (2013.01); *A61F 2002/065* (2013.01); *A61F 2002/075* (2013.01); *A61F 2220/005* (2013.01); *A61F 2230/0095* (2013.01)

(58) Field of Classification Search
CPC ... A61F 2/07–2002/075; A61F 2002/065–067; A61F 2210/0057; A61F 2250/001; A61F 2250/0065; A61F 2250/0012; A61F 2250/0018; A61F 2250/0028; A61F 2250/0029
See application file for complete search history.

(56) References Cited

U.S. PATENT DOCUMENTS

| | | | |
|---|---|---|---|
| 5,290,305 A | 3/1994 | Inoue | |
| 5,507,767 A * | 4/1996 | Maeda | A61F 2/88 606/198 |
| 5,723,004 A * | 3/1998 | Dereume | A61F 2/07 623/1.35 |

(Continued)

FOREIGN PATENT DOCUMENTS

| | | |
|---|---|---|
| EP | 1095635 A1 | 5/2001 |
| GB | 2516928 A | 2/2015 |

(Continued)

OTHER PUBLICATIONS

European Patent Office, Extended European Search Report Issued in Application No. 15201175.5, dated Sep. 20, 2016, Germany, 9 pages.

(Continued)

*Primary Examiner* — Paul B Prebilic
(74) *Attorney, Agent, or Firm* — Alleman Hall Creasman & Tuttle LLP

(57) ABSTRACT

This invention provides a stent-graft that has both shape-maintainability and flexibility, and when implanted in a living body, the stent-graft performs its intended functions for a considerably long period of time relative to conventional stent-grafts, without causing conflict. The stent-graft comprises a stent comprising multiple elastic rings and a graft. An auxiliary elastic wire whose rigidity is lower than that of the stent is arranged at the end-part of the graft, and the auxiliary elastic wire is connected to the multiple elastic rings at the opening part.

14 Claims, 17 Drawing Sheets

(56) References Cited

U.S. PATENT DOCUMENTS

| | | | | |
|---|---|---|---|---|
| 5,827,321 | A | * | 10/1998 | Roubin ............... A61F 2/91 606/195 |
| 5,843,162 | A | | 12/1998 | Inoue |
| 5,879,370 | A | * | 3/1999 | Fischell ............. A61F 2/844 606/198 |
| 5,925,076 | A | | 7/1999 | Inoue |
| 5,976,179 | A | * | 11/1999 | Inoue ................. A61F 2/07 606/194 |
| 6,013,854 | A | * | 1/2000 | Moriuchi ............ A61F 2/91 606/194 |
| 6,273,917 | B1 | * | 8/2001 | Inoue ................. A61F 2/07 623/1.15 |
| 6,635,080 | B1 | * | 10/2003 | Lauterjung ......... A61F 2/07 623/1.13 |
| 7,763,063 | B2 | * | 7/2010 | Arbefeuille ........ A61F 2/07 623/1.11 |
| 2001/0020181 | A1 | * | 9/2001 | Layne ................ A61F 2/07 623/1.13 |
| 2004/0215319 | A1 | * | 10/2004 | Berra ................. A61F 2/07 623/1.13 |
| 2010/0174357 | A1 | * | 7/2010 | LeMaitre ........... A61F 2/07 623/1.15 |
| 2012/0239137 | A1 | * | 9/2012 | Heuser ............... A61F 2/07 623/1.16 |
| 2015/0127086 | A1 | | 5/2015 | Sueda et al. |

FOREIGN PATENT DOCUMENTS

| | | |
|---|---|---|
| JP | 03236836 A | 10/1991 |
| JP | 2001224610 A | 8/2001 |
| JP | 2001511044 A | 8/2001 |
| JP | 2011502572 A | 1/2011 |
| JP | 2011177520 A | 9/2011 |
| WO | 9636387 A1 | 11/1996 |
| WO | 9834668 A1 | 8/1998 |
| WO | 0067674 A1 | 11/2000 |
| WO | 2007022495 A1 | 2/2007 |
| WO | 2009058369 A1 | 5/2009 |
| WO | 2013129445 A1 | 9/2013 |

OTHER PUBLICATIONS

Japanese Patent Office, Office Action Issued in Application No. 2015138551, dated Jan. 24, 2019, 7 pages.

* cited by examiner

STENT-GRAFT

FIELD OF THE ART

This invention relates to a stent-graft intended for implantation in a living body.

BACKGROUND ART

For a stent-graft implanted inside of a blood vessel such as an artery, a certain degree of shape-maintainability, also referred to as 'rigidity' or 'stiffness,' is required in order to avoid contingent transformations of the stent-graft, such as excessive dents or bending, owing to a movement of the blood vessel or a change of blood flow/blood pressure after the stent-graft has been implanted in the blood vessel. At the same time, a degree of 'flexibility' is also required in order for a stent-graft to be able to tightly attach to an inner wall of the blood vessel, and to follow a possible movement from expansion or shrinkage of the blood vessel.

Stent-grafts that place emphasis on shape-maintainability are known as 'stiff' stent-grafts. One example of a 'stiff' stent-graft is the so-called 'z stent' that is comprised of an elastic metal stent surrounding a tubular graft in a triangular wave form, as disclosed in patent document 1. A second example of a 'stiff' stent-graft is a stent-graft having a rhombic mesh structure, as disclosed in patent document 2.

However, when using a 'stiff' stent-graft, it can be difficult to get the stent-graft to flexibly follow the movement of the blood vessel, or to follow the form of a curve-shaped blood vessel. These shortcomings can lead to poor adhesive properties between the stent-graft and the blood vessel that may result in blood entering gaps between the stent-graft and the inner wall of the blood vessel. In addition, in the case of the 'z type' stent-graft there is a chance for a pointed part to form in a bent stent that might break or otherwise damage the blood vessel.

On the other hand, a stent-graft disclosed in the patent document 3 is known as a 'flexible type' stent-graft that places emphasis on 'flexibility.' This stent-graft has an arrangement that is referred to as a 'helical type,' wherein a tubular graft is supported by a stent comprising multiple elastic rings arranged at predetermined intervals.

The 'flexible type' stent-graft has high adhesive properties to the blood vessel; however, due to movement of the blood vessel or due to changes of the blood flow/blood pressure, there exists a tendency with flexible stent-grafts for the opening of the stent-graft to tilt and become diagonally inclined, as opposed to perpendicular, in relation to the axial direction of the blood vessel (hereafter referred to as being diagonally inclined). In the event that an opening of a stent-graft becomes diagonally inclined, a gap is formed between the stent-graft and the inner wall of the blood vessel. Consequently, blood might enter the gap, or the stent-graft might move as a result of being pushed out of place by the blood entering the gap. Furthermore, in the event that the opening of a stent-graft is diagonally inclined, an interval between some rings located at the vicinity of the opening (end-part) on one side surface of the rings may become shorter than an interval between the same rings on the opposite side surface.

In the event that the above-mentioned problems occur, it is frequently necessary to perform corrective treatment on an already implanted stent-graft, or to conduct a complete replacement of a faulty stent-graft.

In light of the above, an idea of a 'hybrid type' stent-graft that combines both 'flexibility' and 'stiffness' was created and is disclosed in patent document 4 and in patent document 5. These 'hybrid type' stent-grafts have an arrangement wherein 'z-type' arrangements are used only for the two opposite end-parts of the stent-graft, while a 'helical-type' arrangement is used in a middle part of the stent-graft.

A practical problem that arises with the use of 'hybrid type' stent-grafts, as the ones described in patent documents 4 and 5, is that due to their structure, it is questionable whether or not these stent-grafts can in fact be transported with conventional unobtrusive methods to an affected target area. This problem is described in detail below.

Folding a 'hybrid-type' stent-graft, such as the ones described in patent documents 4 and 5, in a radial direction for the purpose of housing it in a delivery sheath can pose a challenge. This is because when the 'z-type' end-parts, and 'helical-type' middle parts are made to shrink in the radial direction, they fold in a substantially different manner, which leads to conflicting forces that resist one another along the body of the hybrid stent-graft, and particularly at the sections of the stent graft where the 'z-type' parts and 'helical-type' part meet.

The 'z-type' parts of the stent-graft have a considerably high rigidity or shape maintainability, therefore folding the 'z-type' parts in the radial direction is done by forcing toward each other the zig-zagging wires, whose walls appear as mountains and valleys, to be substantially parallel to each other. Thus when the 'z-type' parts of the stent are folded they exert a pulling force in the radial direction.

On the other hand, folding the 'helical type' part of the 'hybrid type' stent-graft in the radial direction involves folding the 'helical type' part of the stent-graft in what is referred to as a saddle-shape. The saddle-shape inevitably forces the helical part of the stent-graft to transform in both an axial direction as well as a radial direction. This movement in the axial direction conflicts with the rigid structure of the 'z-type' parts of the stent-graft.

Therefore, in the case of folding the 'hybrid-type' stent-graft, as described in the patent documents 4 and 5, in order to shrink the stent-graft in the radial direction, a discrepancy occurs as follows. The axial movement of the 'helical type' part of the hybrid stent-graft conflicts with the axial movement from the 'z-type' parts of the 'hybrid-type' stent-graft. As a result, with consideration of the conflicting forces described above, it can be expected that folding the 'hybrid-type' stent-grafts described in documents 4 and 5 will be extremely difficult in reality. Some degree of folding and shrinking of the stent-graft in the radial direction is likely possible with the exertion of force, but even under severe pressure, the diameter of the folded hybrid stent-graft would likely be too large to be housed in a delivery sheath for delivering the stent-graft to an affected target area.

i. In support of the above, it is worth noting that the documents 4 and 5 do not disclose any detailed view of their respective hybrid stent-grafts being housed in a delivery sheath.

PRIOR ART DOCUMENTS

Patent Document

Patent document 1: WO2007/022495
Patent document 2: WO2013/129445
Patent document 3: WO96/36387
Patent document 4: Japanese Unexamined Patent Application Publication No. 2011-177520

Patent document 5: Japanese Translation of PCT International Application Publication No. JP-T-2011-502572

DISCLOSURE OF THE INVENTION

Problems to be Solved by the Invention

The present claimed invention intends to solve all of the problems described above, with the main objective of the invention being to provide a stent-graft that offers both 'flexibility' and 'shape-maintainability' without a tradeoff between these characteristics, and that when implanted in a living body, performs its intended functions for a considerably long period of time relative to conventional stent-grafts, without causing conflict.

Means to Solve the Problems

More specifically, the stent-graft in accordance with this invention comprises a graft of a tubular shape and multiple elastic rings intermittently arranged in an axial direction of the tubular shape spanning across both end-parts of the graft, and housed in a delivery sheath with each of the elastic rings being transformed into a saddle-shape, and the graft being folded in accordance with the transformation of the elastic rings, and it is characterized by being provided with an auxiliary elastic wire, whose rigidity is lower than that of the elastic rings, and the auxiliary elastic wire is connected, directly or through the graft, to the multiple elastic rings arranged at the end-parts of the graft.

In accordance with this arrangement, even if a force in the axial direction by the blood flow is partially applied to an opening edge of the stent-graft, since the auxiliary elastic wire keeps a pitch between the elastic rings arranged in the vicinity of the opening (end-part) at a predetermined interval, the opening edge is not likely to tilt into a position where it becomes diagonally inclined, and it is possible to prevent the occurrence of a diagonally inclined opening.

In addition, since the auxiliary elastic wire is lower in rigidity than the elastic ring and is easily transformed when subjected to a force from the side surface, the stent-graft is bent flexibly according to the movement and curvature of the blood vessel.

In accordance with this arrangement, it is possible to prevent blood leakage into gaps that may potentially form between the graft and the wall of the blood vessel, and to prevent an unexpected move of the stent-graft inside the blood vessel, without jeopardizing the characteristics of the 'flexible' stent-graft, such as a satisfactory adhesiveness to the walls of the blood vessel or the flexibility of the elastic rings. As a result of this, it is possible for the stent-graft, having been implanted in a living body, to perform intended functions for a considerably long period of time without causing conflict.

Furthermore, since the rigidity of the auxiliary elastic wire is lower than that of the elastic ring, the auxiliary elastic wire will not disturb the transformation of the graft when the elastic ring is folded into a saddle shape. This configuration also makes it possible to fold the stent-graft and shrink its diameter in the radial direction so that it can be housed easily in a delivery sheath.

In order to significantly reduce the possibility that the opening will become diagonally inclined, it is preferable that the auxiliary elastic wire is comprised of multiple first wire elements intermittently arranged in a circumferential direction of the graft, and that each of the first wire elements is connected to the multiple elastic rings arranged at the end-part of the graft in a condition of intersecting with each of the multiple elastic rings.

The auxiliary elastic wire may comprise multiple non-connected first wire elements alone. In such an arrangement, however, there exists a high risk that the blood vessel might get damaged by a distal end of a first wire element. In addition, this arrangement requires that the rigidity of each first wire element be increased considerably in order to prevent the end-parts from becoming diagonally inclined, which might hinder the stent-graft from being folded.

In order to solve this problem, it is preferable that the auxiliary elastic wire is an endless annular shape (a continuous loop having no ends) that surrounds the graft so as to repeat a concave portion and a convex portion in the axial direction of the tubular shape, and the auxiliary elastic wire comprises multiple second wire elements, each of which forms the concave portions and the convex portions, and multiple first wire elements, each of which links the concave portions and the convex portions.

The reason for the above described configuration is that the auxiliary elastic wire comprised of flexible, continuously connected first and second wire elements achieves flexibility due to the material it is made of, along with structural rigidity due its three-dimensional structure. 'Shape-maintainability' or a shape-recovering function of the end-part is therefore increased by support from the auxiliary elastic wire, and a function of preventing tilting that may cause the opening to be diagonally inclined relative to the axial direction of the blood vessel is also enhanced. In addition, since the auxiliary elastic wire is an endless annular shape, free of sharp or pointed edges, it is possible to reduce the likelihood of damage being caused to the blood vessel. Furthermore, since the shape-maintainability of the stent-graft is improved due to the three-dimensional structure of the auxiliary elastic wire, it is possible to minimize the rigidity of the auxiliary elastic wire, resulting in an effect whereby the stent-graft can be folded with ease and the diameter of the folded stent-graft can be made small enough to be housed in a delivery sheath.

When the elastic ring is folded, the most significant transformation takes place at the tops of the curved portions of the elastic ring and in their vicinity. If there exists resistance to transformation of curved portions in the outermost elastic rings located at the end-parts of the stent graft, there might be a problem in folding or expanding the elastic ring, and, consequently, a problem in folding the stent-graft. In order to avoid this problem, it is preferable that the auxiliary elastic wire is arranged at a position avoiding both a top of the curved portion of the elastic ring, arranged at each of the end-parts of the graft, and a vicinity thereof.

As a preferable embodiment, eight pieces of the first wire elements and eight pieces of the second wire elements are provided.

As a concrete arrangement to ensure that the auxiliary elastic wires avoid the tops of the curved portions of the elastic rings arranged at each of the end-parts and their vicinity, the top of the curved portions of the elastic ring are located between adjacent convex parts of the auxiliary elastic wire.

In order to ensure avoidance of the auxiliary elastic wire being arranged at the top of the curved portion of the elastic rings arranged at each of the end-parts or in their vicinity without fail, it is preferable that a length in the circumferential direction of the second wire element, which forms the concave portion that avoids the elastic ring, is set to be longer than a length in the circumferential direction of the second wire element that forms the convex portion.

In order to improve a three-dimensional structural strength of the auxiliary elastic wire and to avoid forming a pointed corner, so as to prevent contingent damage to the blood vessel, it is preferable that the first wire elements extend generally along the axial direction of the tubular shape and that the second wire elements are connected to the adjacent first wire elements while curving smoothly between the first wire elements.

In order to facilitate bending or stretching of the stent-graft along the axial direction of the tubular shape so as to improve adhesiveness of the stent-graft to the blood vessel and to prevent a contingent move of the stent-graft inside of the blood vessel after the stent-graft has been implanted, it is preferable that the graft is provided with multiple surrounding crease lines at a predetermined pitch in the axial direction of the tubular shape, and that the pitch of the surrounding crease lines be set to be smaller than the pitch of the elastic rings.

Past experience has shown that there are cases where the blood vessel corresponding to a rear end-part (a downstream side in the blood vessel) of the stent-graft might get damaged after the stent-graft has been implanted. Upon keen examinations made by the present inventor, it has been found that if an opening diameter of the stent-graft arranged in the downstream side of the blood vessel is set to be smaller than a diameter of a middle part of the stent-graft, it is possible to substantially reduce the likelihood of such damage to the blood vessel. This effect is especially noticeable in treatment of aortic aneurysms.

Conventionally, in the case of an aneurysm of the aortic arch portion or a dissociation of arch aortic aneurysm, it is difficult to implant a stent-graft via a catheter. Therefore, in such cases an artificial blood vessel is commonly implanted by means of an operation for a thoracotomy. However, with an appropriate stent-graft such as the one disclosed below it is possible to achieve the remarkable effect of implanting a stent-graft into an aortic arch portion by means of a catheter. Such an appropriate stent-graft is a stent-graft that comprises a main tube that is mounted on the aortic arch portion so as to cover the inner walls of an aortic aneurysm from the inside, and that further comprises a diverging tube that diverges from the graft and that is inserted into a blood vessel that diverges from an aortic arch portion. Such a stent-graft may be made with multiple diverging tubes on the upstream side of the main tube, so as to be inserted into one or more arteries (e.g., left subclavian artery, left common carotid artery, brachiocephalic artery) that diverge from the aortic arch portion.

The stent in accordance with the present claimed invention is not limited to the above-mentioned configuration that comprises multiple elastic rings, and may comprise an elastic and helical ring as well.

Effect of the Invention

In accordance with this invention, since the auxiliary elastic wire keeps the pitch between the elastic rings arranged in the end-part, it is possible to prevent a contingency such that the opening of the stent-graft is accidentally tilted and becomes diagonally inclined relative to the axial direction of the blood vessel.

In addition, since the auxiliary elastic wire is lower in rigidity than the elastic ring, the auxiliary elastic wire is easily transformed when it is subjected to a force in the radial direction, and the stent-graft can be bent flexibly and conform to the curvatures of the blood vessel.

As a result of this, it is possible to prevent blood leakage into gaps, and to prevent an unexpected move of the stent-graft, without impairing characteristics of the 'flexible' stent-graft, such as sufficient adhesiveness or flexibility of the elastic rings to adhere to the inner wall of the blood vessel. It is therefore possible for the stent-graft to be used for a long period of time (more than 10 years) without conflict.

In addition, since the rigidity of the auxiliary elastic wire is less than that of the elastic ring, the auxiliary elastic wire will not disturb the elastic ring from transformations such as when it is being bent or folded. It is also possible to fold the elastic ring to be small and narrow, and to house the folded stent-graft in the delivery sheath easily.

BEST MODES OF EMBODYING THE INVENTION

First Embodiment

Figure 1:
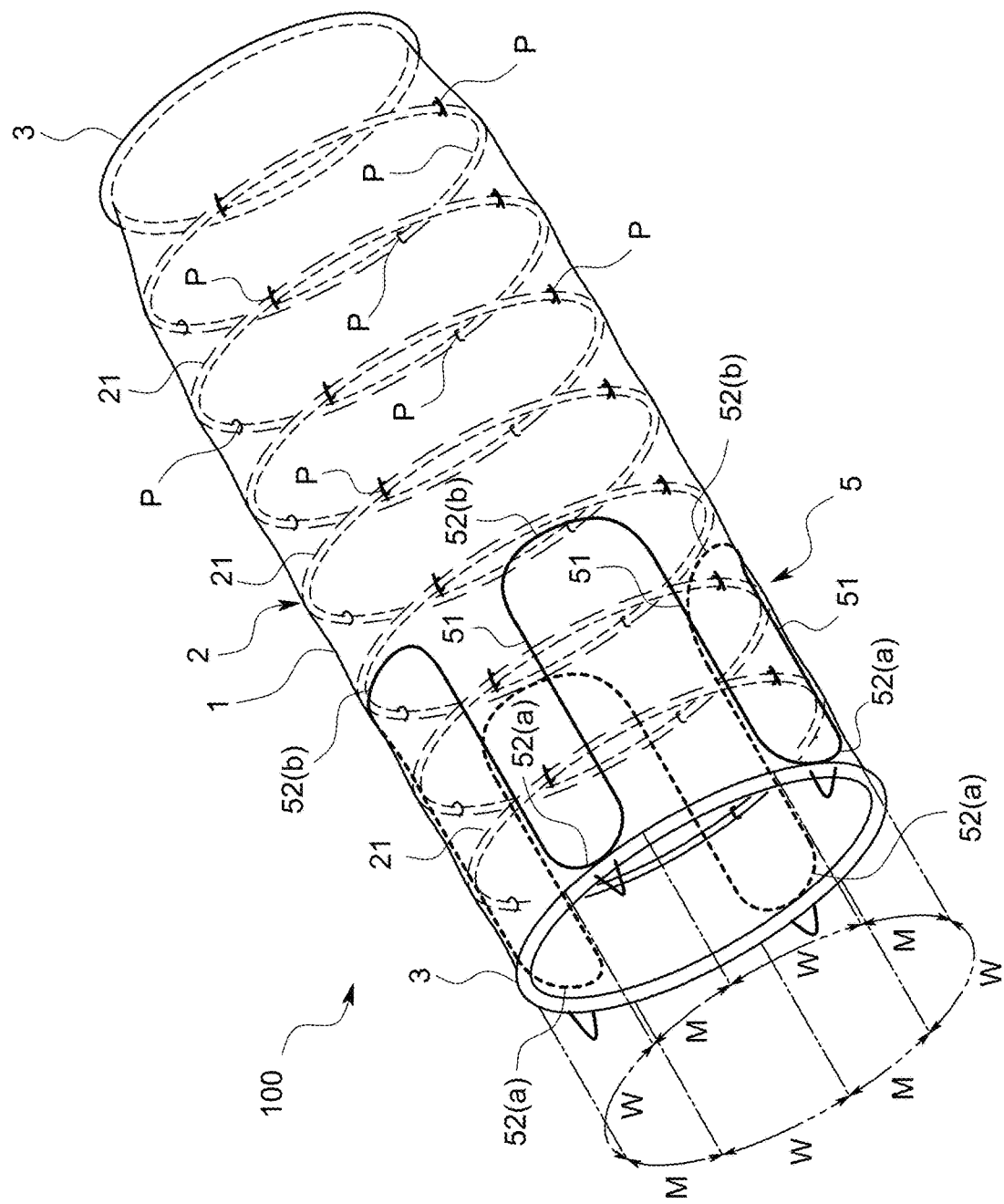
FIG. 1 is a general view showing an expanded state of a stent-graft in accordance with a first embodiment of this invention.
Figure 2:
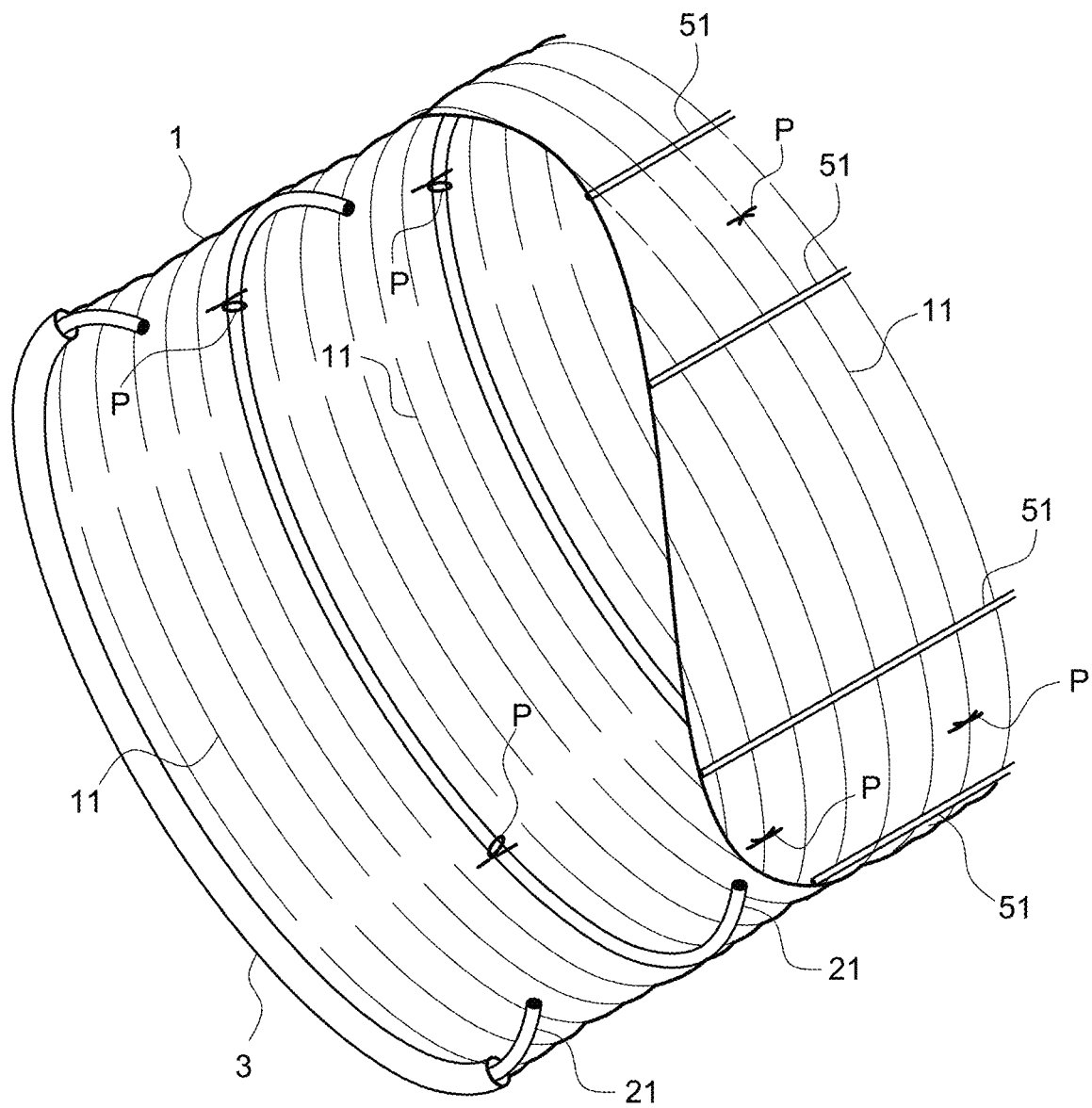
FIG. 2 is a partially broken perspective view of the stent-graft in accordance with this embodiment.

A stent-graft 100 in accordance with this embodiment comprises a graft 1 (an artificial blood vessel) of a tubular shape whose ends are both open, and a stent 2 mounted on the graft 1 in order to keep the shape of the graft 1 as shown in FIG. 1 and FIG. 2. The stent-graft 100 is transported to and released inside a blood vessel having a lesion portion, such as a thoracic aorta aneurysm or an abdominal aorta aneurysm, via a catheter 200 (shown in FIG. 6 through FIG. 8). Then the stent-graft 100 sticks to an inner wall of a blood vessel due to its own tendency to expand in a radial direction and due to the force exerted by blood pressure in the blood vessel. The stent-graft 100 then functions as an artificial blood vessel by covering the blood vessel walls from the inside.

The graft 1 is formed into a tubular shape made of a resin sheet that is durable and has little likelihood of reacting with living tissue. As shown in the partial break view of FIG. 2, the graft 1 is configured in a bellow shape, wherein multiple creases 11 are formed along a circumferential direction of the tubular shape in advance. This configuration makes it easy for the graft 1 to curve, shrink and stretch along the axial direction of the tubular shape. The resin sheet may be a material such as a knit fabric of fibers, a non-woven fabric, or a porous sheet. In addition, a surface of the sheet constituting the graft 1 may be provided with a coating treatment of an antithrombotic material such as heparin, collagen, acetylsalicylic acid, or gelatin.

The stent 2 comprises multiple elastic rings 21, and the multiple elastic rings 21 are arranged to have a uniform predetermined interval (pitch) in between them, all across from one opening end of the graft 1 to the other. Although uniform predetermined intervals are applied in this embodiment and are generally the norm in the field, non-uniform intervals may also be applied.

The elastic ring 21 is of a circular shape having a predetermined elasticity, such as, for example, a metal core covered by a resin film. The metal core is formed of a multiple-strand wound metal wire with an ultra-fine diameter (not shown in drawings). Metals such as stainless steel, tantalum, titanium, platinum, gold, tungsten and their alloys are suggested as possible materials of the core. The core made of the multiple-strand wound metal wire with the ultra-fine diameter improves durability in comparison with a core made of a single-strand wound metal wire. In addition, even in the event that the elastic ring 21 is broken, the core comprised of the multiple-strand wound metal wire will break only partially, making it possible for a broken elastic ring 21 to not lose its function immediately. Similarly to the graft 1, the elastic ring 21 may be provided with a coating treatment of an antithrombotic material.

It is preferable that the elastic ring 21 is mounted on the graft 1 only at specific points along its circumference, and is thus in a state where it is at least partially free to move independently of the graft. The reason is that when the elastic ring 21 is mounted on the graft in such a partially free state it becomes possible to smoothly fold or expand the stent-graft 100. Conversely, if the graft 1 and the elastic ring 21 were arranged in a state where the elastic ring 21 is continuously fixed to the graft 1 along the entire circumference of the elastic ring 21, even a slight bending would not be possible due to rigidity and resistance, and it would become difficult to fold the stent-graft 100 into layers, or difficult to fold the stent-graft 100 into a compact form (especially in a radial direction). Consequently, a contingency may occur such as the stent-graft 100 failing to expand in the blood vessel when released from the catheter 200.

In order to avoid this problem, only certain portions (four portions for each elastic ring 21 in this embodiment) of the elastic ring 21 are sewn to the graft by, for example, a sewing thread (P), that fixes them intermittently to the graft 1. A detailed explanation of the sewn portion is described later in this document.

The elastic ring 21 is mounted on an inner circumferential surface of the graft 1. It is a matter of course that the elastic ring 21 may be mounted on an outer circumferential surface of the graft 1. However, in accordance with an arrangement where the elastic ring 21 is mounted on the outer circumferential surface of the graft 1, it is necessary to increase the number of portions where the elastic ring 21 is sewn to the graft 1 in order to prevent the graft 1 from being partially detached from the elastic ring 21 and from being bent toward the inside and becoming diagonally inclined relative to the blood vessel. However, with the increase of portions where the graft and elastic ring are sewn together, the degree of freedom in the movement of the elastic ring 21 relative to the graft 1 is prone to impairment, and the time required for manufacturing the stent-graft 100 increases significantly as well. Furthermore, since in this configuration the elastic ring 21 directly abuts the blood vessel, the blood vessel might get damaged.

Therefore, in this embodiment, the elastic ring 21 is mounted on the inner circumferential surface of the graft 1 and the number of portions of the elastic ring 21 sewn to the graft 1 is minimized. Consequently, breaking of the blood vessel is also prevented.

Special attention must be given to the elastic rings 21 that are arranged at an upstream end (hereinafter also called a front-end) and a downstream end (hereinafter also called a rear-end) of the graft. If the elastic rings 21 located at the front-end and the rear-end are sewn intermittently to the graft 1 only at certain portions of the graft 1, similarly to the other elastic rings 21, there is a risk that portions of the graft 1 will turn at least partially inside-out or outside-in at the areas where the graft and the elastic ring 21 are not sewn together. This in turn may lead to leakage of blood from the portion that has been turned inside-out or outside-in.

Thus, in this embodiment, as shown in FIG. 1 and FIG. 2, the elastic rings 21, arranged at both the front-end and rear-end of the graft 1, are housed in a circular housing tube 3, which is made of the same sheet material as the graft 1. The elastic rings 21 are completely engulfed by the circular housing tube 3, but are configured to have some wiggle room inside the circular housing tube 3, making it possible for the rings 21 to slide in a circumferential direction inside of the circular housing tube 3. Furthermore, the housing tube 3 is continuously sewn onto the end-parts of the graft 1 at multiple portions. In accordance with this arrangement, the elastic rings 21 can be continuously mounted in the circumferential direction on the graft 1 while allowing the elastic rings 21 some movement, or wiggle room, in the circumferential direction relative to the graft 1.

The stent-graft 100, having the above-mentioned arrangement, can be made to be in a folded state wherein the diameter of the stent-graft 100 is shrunk, in order to make it possible for it to be housed in a delivery sheath (a catheter 200).

Figure 3:
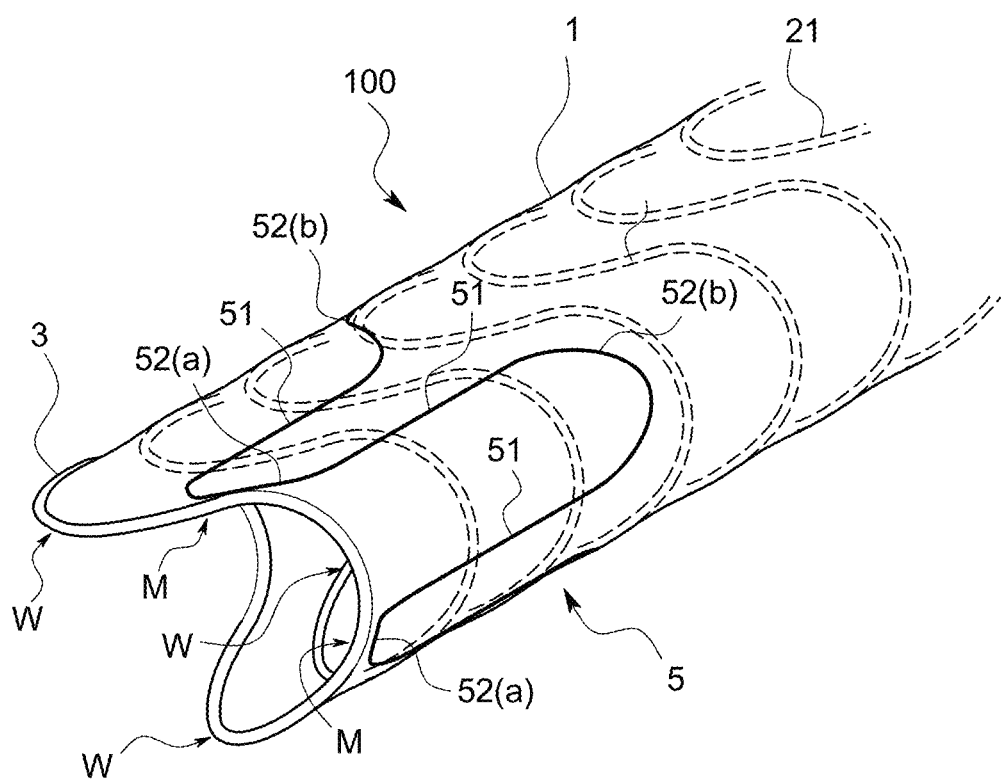
FIG. 3 is a view showing the stent-graft in a state where it is halfway folded toward a folded state in accordance with this embodiment.
Figure 4:
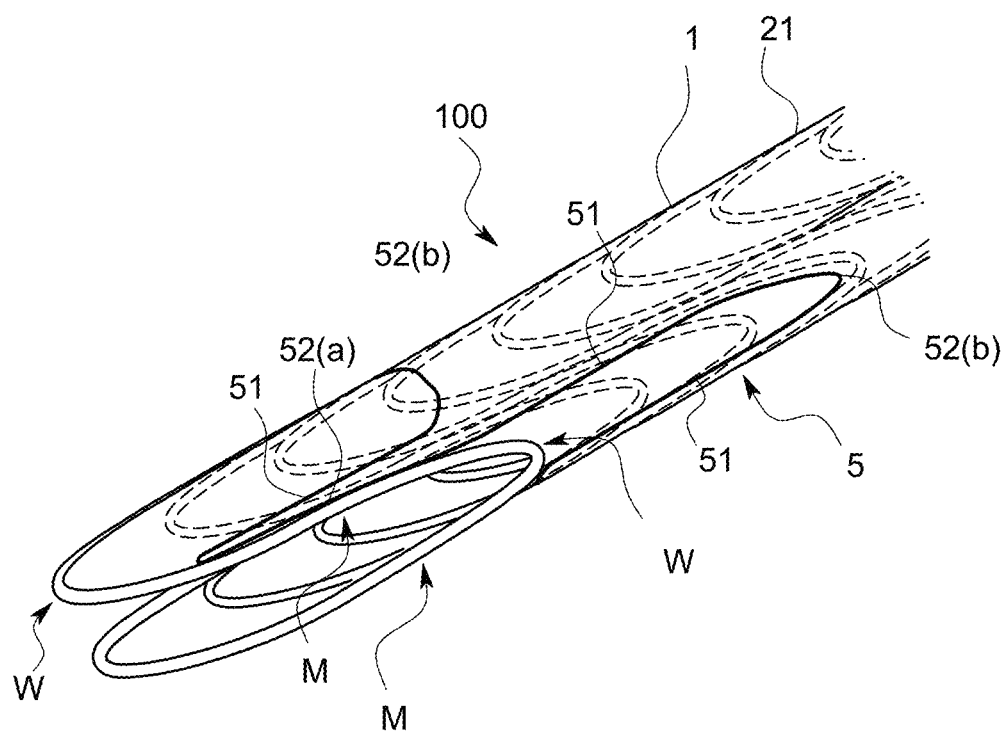
FIG. 4 is a perspective view showing the folded state of the stent-graft in accordance with this embodiment.

In the folded state, all of the elastic rings 21 are bent in the same direction in a saddle-shape, and the graft 1 is also transformed in accordance with the transformation of the elastic rings 21. The term "bent in a saddle-shape" means that the elastic ring 21 is bent in a double-folded state so as to make four alternating mountain parts and valley parts, as shown in FIG. 3 and FIG. 4. A curved portion of the elastic ring 21, that forms the mountain parts and the valley parts in the state of being transformed into the saddle shape, is called a curved portion (W). The other portion of the elastic ring 21 that is located between the curved portions (W) and whose curvature is limited is called a middle portion (M).

As is clear from FIG. 3 and FIG. 4, in a process where the elastic wire 21 is transformed between the expanded state and the folded state, the curved portions (W), and particularly the center sections of the curved portions (W), which may be also understood as the peaks of the mountain parts and the bottoms of the valley parts, are transformed to the greatest degree, while the middle portions (M) are only minimally transformed.

Since the graft 1 is connected to the elastic ring 21 at specific portions, at these portions any movement of the ring forces the graft to transform as well. However, if the graft and the ring are connected at a point such as (W) where the transformation of the ring is significant, a force of resistance to the transformation is to be expected. This resistance may cause problems such as difficulty folding and expanding the stent-graft 100, and particularly a difficulty folding the stent-graft 100 into a state where its diameter is small enough for being inserted into a sheath, such as catheter 200, for application without the use of excessive force that could damage or break the stent-graft 100.

Thus, in this embodiment, in order to solve the problems mentioned above, the graft 1 is sewn to the elastic ring 21 only at portions where the transformation of the elastic ring 21 is the smallest, which is at a center (a center between the top of the mountain part and the bottom of the valley part) of the middle portions (M). However, as mentioned above, this manner of sewing the graft to the elastic rings 21 shall not be applied to the elastic rings 21 that are housed in the housing tubes 3, arranged at both front and rear ends of the stent-graft 100.

Next, a method for transporting the stent-graft 100 to a lesion portion will be explained with reference to FIG. 6 through FIG. 9.

First, the stent-graft 100 is mounted on to a transporting tube 300 that is located inside of the stent-graft 100, and the stent-graft 100 is housed in a distal end-part of the catheter 200 in a folded state. The transporting tube 300 is made of resin and has a hollow body with a sealed distal end part. The transporting tube 300 is set so that the sealed distal end-part projects from the distal end of the catheter 200.

Figure 6:
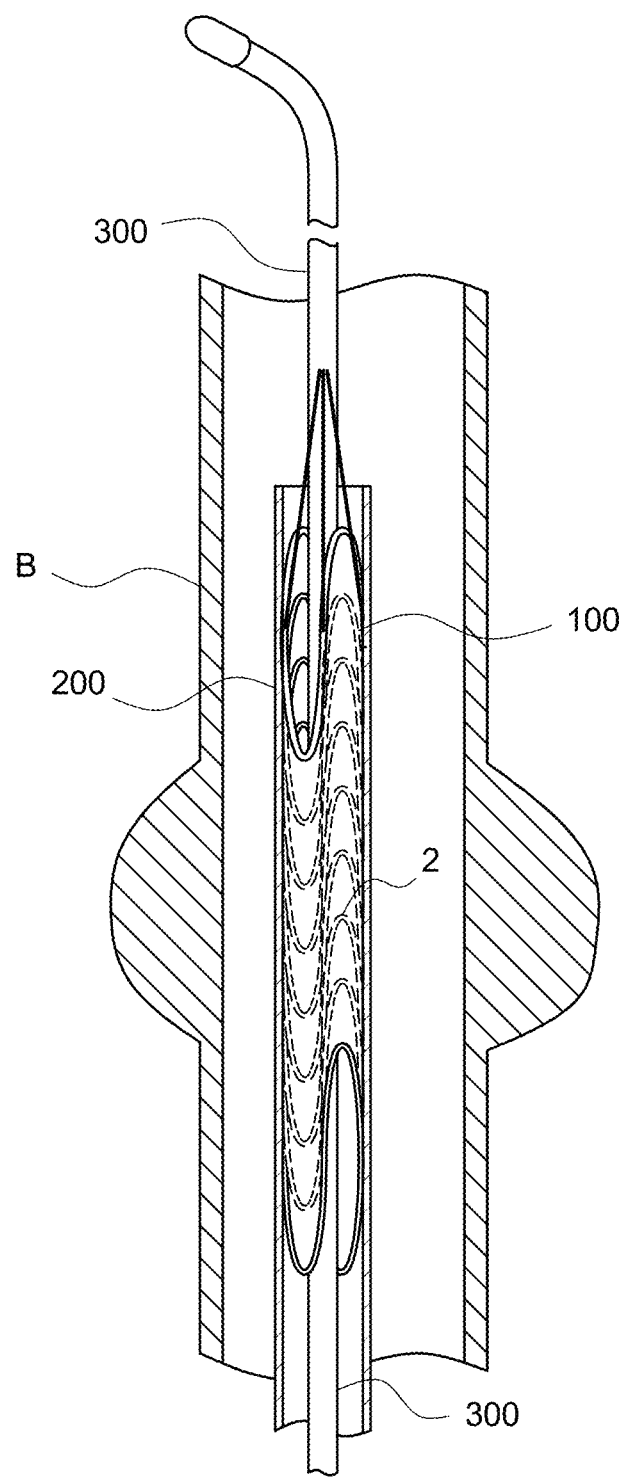
FIG. 6 is an explanatory view to explain a method for transporting and implanting the stent-graft into a portion of a blood vessel with a lesion in this embodiment.

Next, the catheter 200 that houses the transporting tube 300 and the stent-graft 100 is inserted into the blood vessel and is transported inside the blood vessel to a point where the distal end-part of the catheter 200 reaches a lesion portion as shown in FIG. 6.

Figure 7:
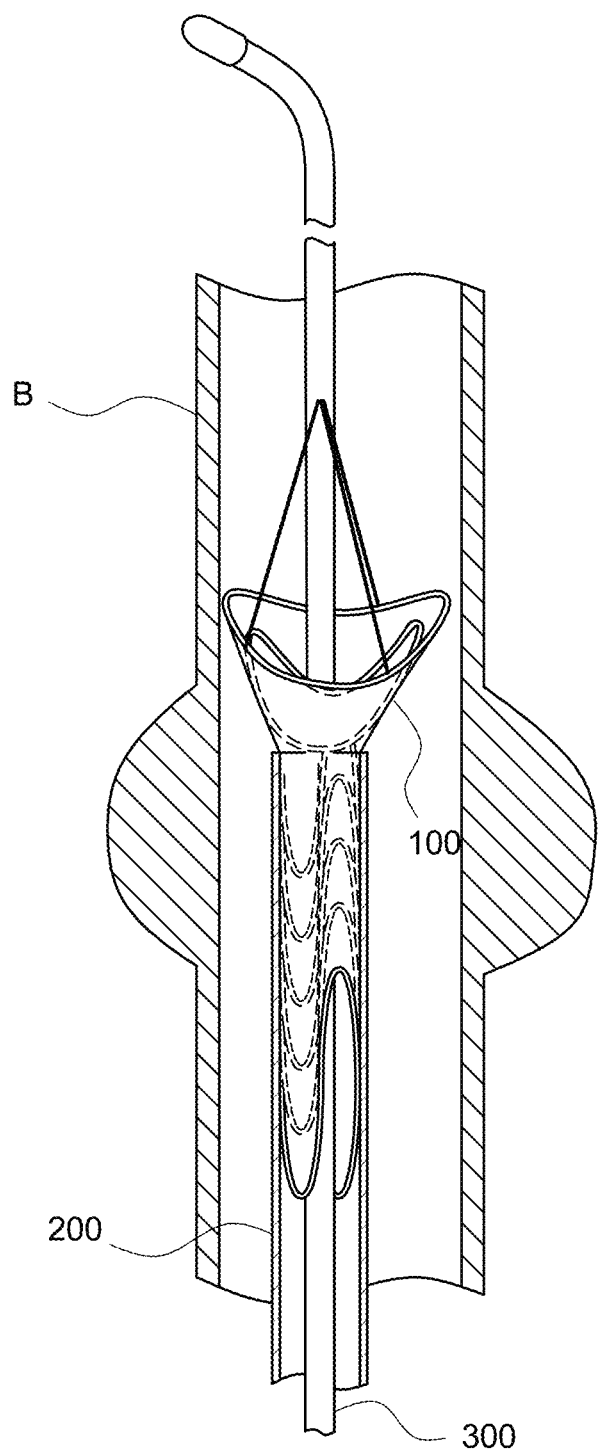
FIG. 7 is an explanatory view to explain a method to transport and implant the stent-graft into a portion of a blood vessel with a lesion in this embodiment.
Figure 8:
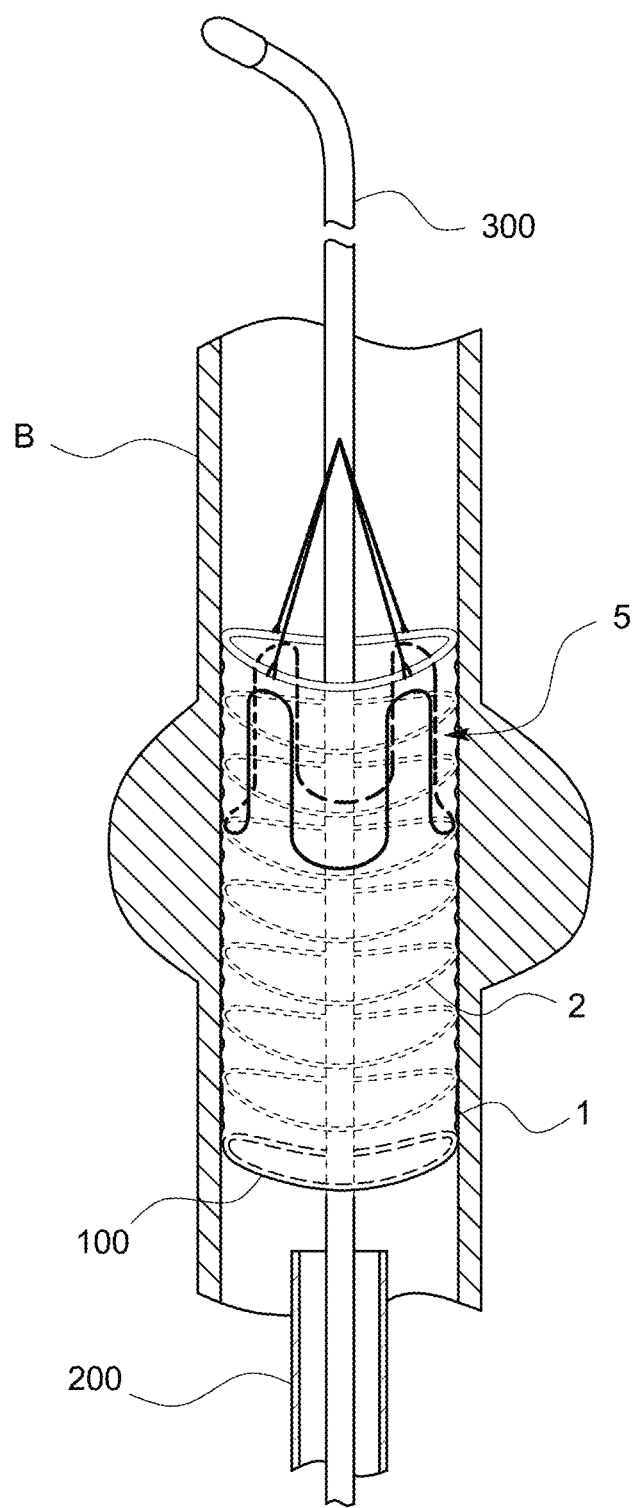
FIG. 8 is an explanatory view to explain a method to transport and implant the stent-graft into a portion of a blood vessel with a lesion in this embodiment.

Next, as shown in FIG. 7 and FIG. 8, the catheter 200 alone is pulled back and the stent-graft 100 is released in the blood vessel. With this procedure, the stent-graft 100 transforms from the folded state to the expanded state wherein its diameter expands due to its own elastic restoring force, and due to the force exerted by blood pressure in the blood vessel, and as the stent graft 100 expands it tightly attaches to the inner wall of the lesion portion in the blood vessel.

Figure 9:
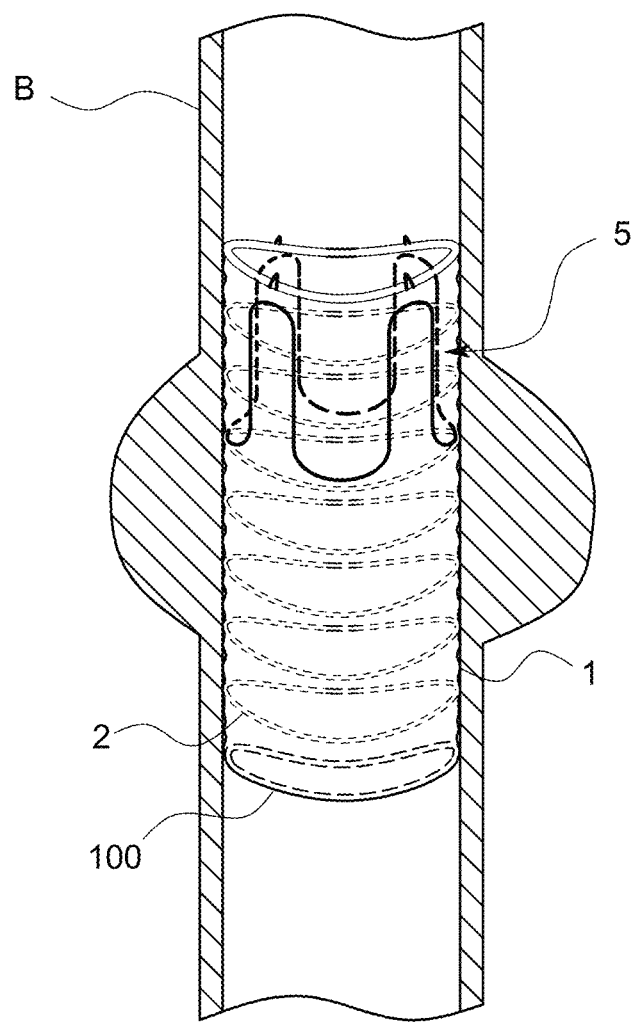
FIG. 9 is an explanatory view to explain a method to transport and implant the stent-graft into a portion of a blood vessel with a lesion in this embodiment.

Finally, as shown in FIG. 9, the expanded stent-graft 100 is dismounted from the transporting tube 300, and the transporting tube 300 and the catheter 200 are retrieved.

The elastic rings 21 are not completely expanded to their fullest extent when the stent graft 100 is in the target blood vessel, as shown in FIG. 8 and FIG. 9. Rather, they remain slightly bent, as in this state they continuously exert an elastic restoring force that securely attaches the graft to the inner wall of the blood vessel, even as the blood vessel expands due to fluctuations in blood pressure. For this purpose, the diameter of the fully expanded elastic ring 21 is set to be slightly larger than an internal diameter of the target blood vessel.

Figure 10:
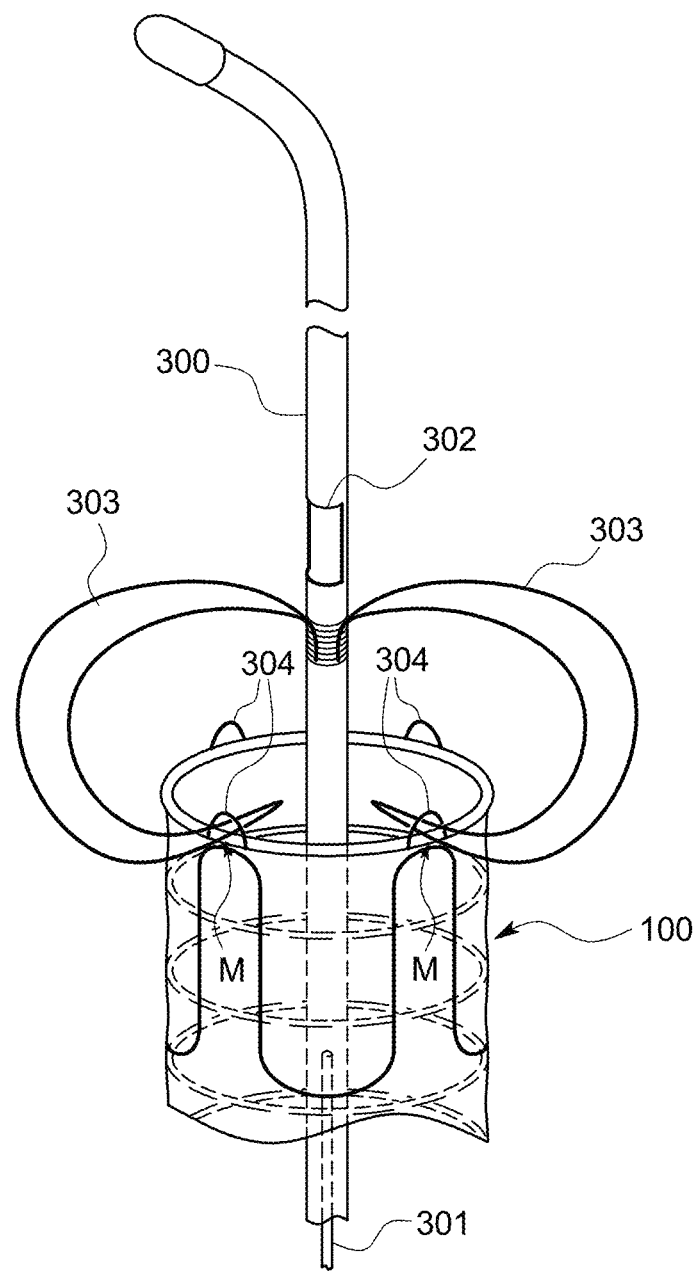
FIG. 10 is an explanatory view to explain a method to mount the stent-graft on a transporting tube in this embodiment.
Figure 11:
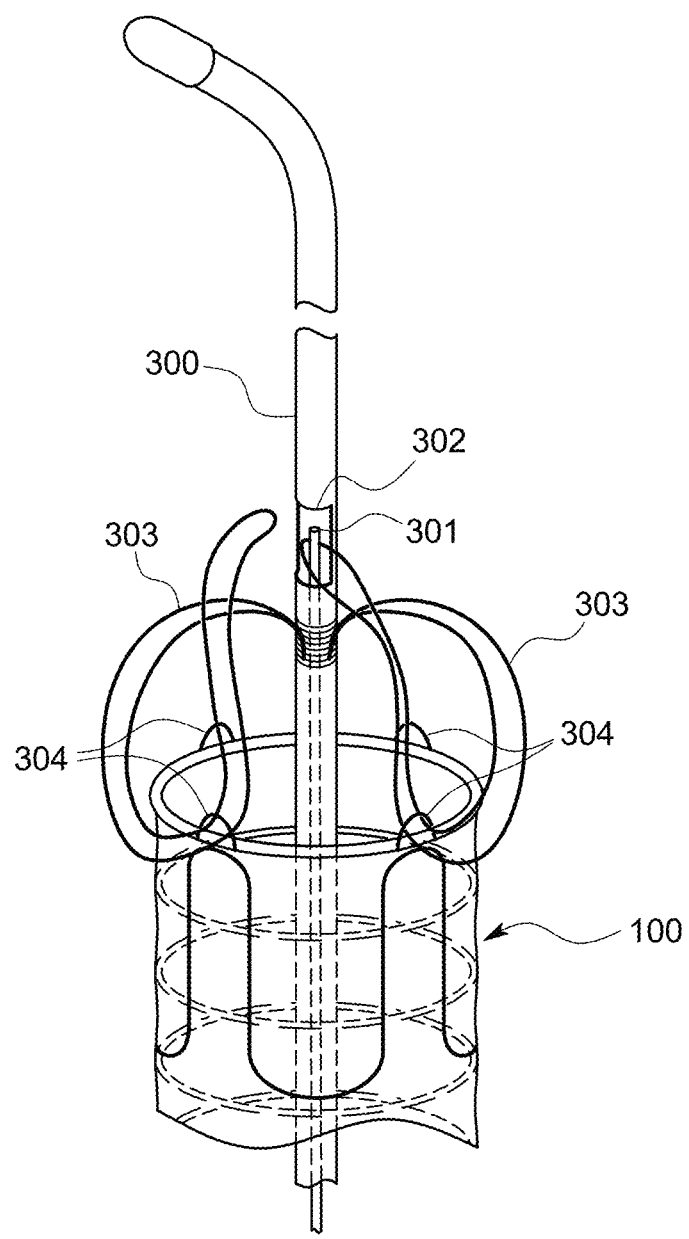
FIG. 11 is an explanatory view to explain a method to mount the stent-graft on a transporting tube in this embodiment.
Figure 12:
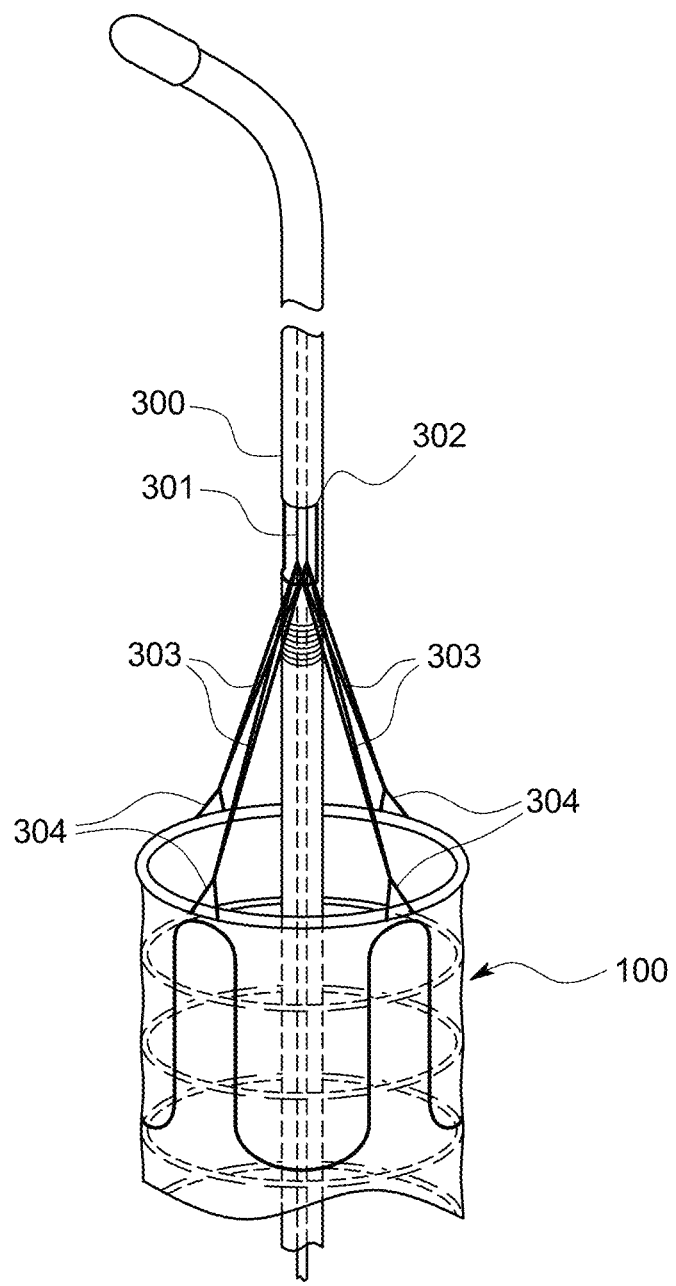
FIG. 12 is an explanatory view to explain a method to mount the stent-graft on a transporting tube in this embodiment.

A structure for mounting or dismounting the stent-graft 100 on or from the transporting tube 300 will be explained. The structure for mounting or dismounting the stent-graft 100 comprises, as shown in FIG. 10 through FIG. 12, a locking wire 301 that passes through the inside of the transporting tube 300, a window 302 arranged on the transporting tube 300, multiple detachable strings 303 (four in this embodiment, only two illustrated in FIG. 10 and FIG. 11 for clarity of presentation) whose proximal end-parts are fixed to the transporting tube 300, and multiple hook bores 304 (four in this embodiment) arranged at an opening edge part of the stent-graft 100.

The locking wire 301 is a steel wire structured to be able to move forward and backward inside of the transporting tube 300 by being pushed or pulled by an operator. The window 302 is formed by cutting away a part of the transporting tube 300. The locking wire 301 located inside of the transporting tube 300 is thus exposed from the window 302.

The detachable strings 303 each have a loop formed, at least at their distal end-part (in this embodiment, the whole of the string 303 is a single endless loop), and the proximal end-part thereof is fixed to the transporting tube 300 at the vicinity of the window 302, (on the side of the window 302 closest to the operator, in this embodiment).

The hook bore 304 is formed by mounting a string formed into a loop on a front end opening edge part of the stent-graft 100.

Next, a process for mounting the stent-graft 100 on the transporting tube 300 will be explained.

First, as shown in FIG. 10, each of the detachable strings 303 has a distal end-part, and each of the distal end-parts is passed through one of the hook bores 304 that are arranged at each of the four positions of the opening end-parts of the stent-graft 100.

On the other hand, the locking wire 301 is operated so as to expose a distal end-part of the locking wire 301 from the window 302 arranged on the transporting tube 300.

Next, as shown in FIG. 11, the loops formed at the distal end-parts of the detachable strings 303, which have been passed through the hook bore 304, are inserted into the window 302 and hooked onto the distal end-part of the locking wire 301. After all of the detachable strings 303 have been successfully hooked onto the locking wire 301, the locking wire 301 is sent upstream inside the transporting tube 300 so as to pass the distal end-part of the locking wire 301 beyond the window 302 until the distal end-part of the locking wire 301 has reached a point along the transporting tube 300 that is downstream of the window 302. In this way, the loops formed at the distal end-parts of the detachable strings 303 that passes through the hook bores 304 are engaged by a middle part of the locking wire 301 that is exposed from the window 302 of the transporting tube 300 so that the stent-graft 100 is mounted on the transporting tube 300 through the detachable strings 303.

To dismount the stent-graft 100 from the transporting tube 300, the locking wire 301 is pulled until the distal end-part of the locking wire 301 reaches the side of window 302 that is closer to the operator, or in other words, an upstream side of the window 302. With this procedure conducted, the loop formed at the distal end of each detachable string 303 is released from the locking wire 301, leaving the stent-graft 100 detached from the transporting tube 300.

The above-mentioned hook bore 304 is arranged adjacent to the middle portion (M) (more concretely, a center of the middle portion (M)). If the hook bore 304 is arranged at this position, a distance from the axis of the stent graft 100 to the hook bore 304 can be kept constant both in the folded state and the expanded state. As a result of this, it is possible for the four detachable strings 303 to maintain a uniform tension on a constant basis. In a case where there are only two detachable strings 303, the hook bores 304 may be arranged at the top of the curved portion (W).

Before the transporting tube 300 and the catheter 200 are retrieved, a balloon (not shown in drawings) may be guided by the transporting tube 300 and transported inside of the stent-graft 100. The balloon can then be inflated so as to ensure that the stent-graft 100 is tightly attached to the inner wall of the blood vessel.

The following is a description of the concrete structure of the stent-graft 100, and the method for transporting and implanting the stent-graft 100 at a target location.

In this embodiment, as is shown in FIG. 1, the auxiliary elastic wire 5, which is thinner than the stent 2 and whose rigidity is lower than that of the stent 2, is mounted (sewn) to surround an outer circumferential surface (at least an outer circumferential surface of a front end-part) of an end-part of the graft 1.

A pitch between the points where the auxiliary elastic wire 5 is mounted (sewn) to the graft 1 is set to be smaller than a pitch between the elastic rings 21.

A concrete explanation will follow.

Figure 5:
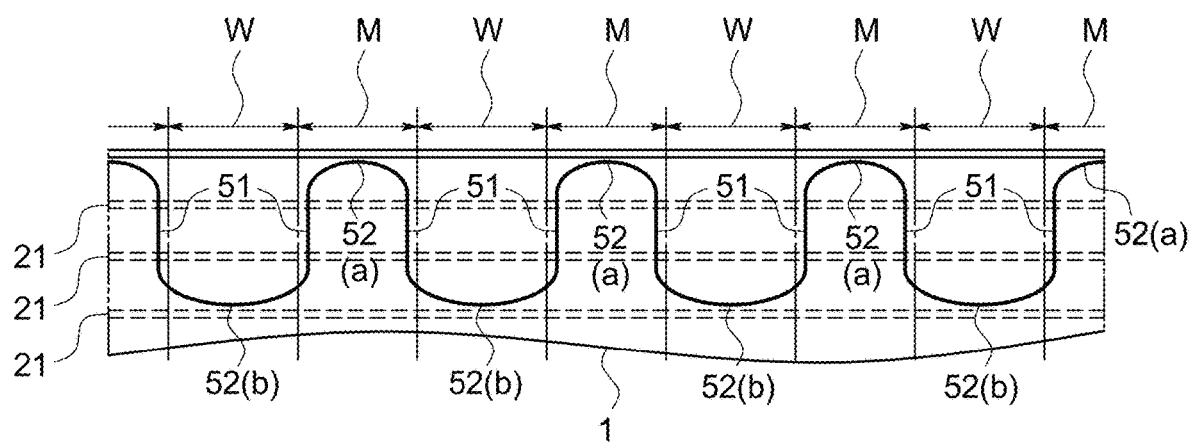
FIG. 5 is a plane expansion view of the stent-graft to explain an auxiliary elastic wire in this embodiment.

A perspective view of the auxiliary elastic wire 5 is shown in FIG. 1 through FIG. 4, and a development view thereof is shown in FIG. 5. The auxiliary elastic wire 5 is an endless annular shape that surrounds the graft 1 in a manner where a repeated pattern of concave portions 52(*b*) and convex portions 52(*a*) are formed. More concretely, the auxiliary elastic wire 5 comprises: eight second wire elements, each of which forms the concave portions 52(*b*) and the convex portions 52(*a*); and eight first wire elements 51, each of which links the concave portions 52(*b*) and the adjacent convex portions 52(*a*).

The first wire elements 51 extend generally along the axial direction of the tubular shape, and are arranged in a state of intersecting with each of the multiple (e.g., two to five) elastic rings 21 located at the end-part of the stent-graft 100. The intervals between the first wire elements 51, each of which are adjacent to each other, is not constant, but rather it repeats an alternating pattern of a wide interval followed by a narrow interval.

The second wire elements 52 include convex portions 52(*a*), and concave portions 52(*b*). The portions 52 (*a*) are formed at the juncture of the distal ends of the narrowly-spaced first wire elements 51, on the opening side of the graft 1. The concave portions 52(*b*) are formed at the juncture of the proximal ends of the widely-spaced first wire elements 51. Both the concave portions 52(*a*) and convex portions 52(*b*) are formed as a curled horseshoe-like shape.

The auxiliary elastic wire 5 is arranged so that the second wire elements 52(*b*) that connect the widely-spaced first wire elements 51, are distal to the ends of the stent-graft 100, while the second wire elements 52(*a*) are proximal to the ends of the stent-graft 100. In other words, the gap between the widely-spaced first wire elements 51 is open on the side nearest to the end of the stent-graft 100.

Furthermore, in this embodiment, the outer diameter of the rear end of the stent-graft 100, arranged in the downstream side of the blood vessel, is set to be smaller than the outer diameter of the middle part thereof, so as to generate a gap between the outer circumference of the opening part of the rear-end of the stent-graft 100 and the blood vessel.

In accordance with the stent-graft 100 having the above-mentioned arrangement, the auxiliary elastic wire 5 produces a shape-maintainability function by means of its three-dimensional structure in the expanded state. Consequently, the auxiliary elastic wire 5 keeps the multiple elastic rings 21, located at the opening part, at a fixed distance from each other, and thus inhibits the opening part of the stent-graft 100 from being tilted into a position where it is diagonally inclined relative to the axial direction of the tubular shape.

A more detailed explanation will follow.

In the event that the stent-graft 100 is provided with the elastic rings 21 alone (without an auxiliary elastic wire 5), a force of the rings 21 to expand in the radial direction and secure the stent-graft to the blood vessel walls is present, though it may not be sufficient to inhibit the elastic rings 21 from being tilted. Particularly at a time when the stent-graft 100 is implanted, or when a contingent force is applied due to blood flow or due to movement of the blood vessel, there is a possibility that some elastic rings 21 arranged at the opening part of the stent-graft 100 will become tilted from an upright predetermined posture relative to the axial direction of the tubular shape. When this occurs, the opening part of the stent-graft 100 becomes tilted relative to the blood vessel and a gap is generated between the stent-graft 100 and the blood vessel, making it possible for blood to leak from the gap, or for the stent-graft 100 to move contingently.

Since the auxiliary elastic wire 5 is mounted on the elastic rings 21 spanning across the multiple elastic rings 21 arranged at the opening part, and since the auxiliary elastic wires 5 support the elastic rings 21 so as not to change the distance between the elastic rings 21, the elastic rings 21 are inhibited from being tilted and are kept in an adequate posture wherein the opening part is generally perpendicular to the axial direction of the tubular shape.

In addition, since the auxiliary elastic wire 5 has a three-dimensional structure of an endless ring shape having concave parts and convex parts in the axial direction of the tubular shape in the expanded state, the auxiliary elastic wire 5 has high shape-maintainability. Due to the high shape-maintainability of the auxiliary elastic wire 5, the structure of the stent-graft 100, particularly the end-parts of the stent-graft 100 which are supported by the auxiliary elastic wire 5, has high shape-maintainability as well, making it difficult to tilt the stent-graft 100 relative to the blood vessel.

While the auxiliary elastic wire 5 improves the shape-maintainability in the expanded state and prevents the opening from being tilted, as mentioned above, it also produces an effect of being flexible so as to easily fold. In other words, the auxiliary elastic wire 5 offers the best of both worlds: shape-maintainability and flexibility to fold that facilitates the folding of the stent-graft 100 as a whole. This is in contrast to prior art, where there tends to be a trade-off between shape-maintainability and flexibility to fold. This is made possible since the three-dimensional structure of the elastic wire 5 produces a degree of shape-maintainability, while the elastic wire can be made of a very flexible material, with a rigidity that is half that of the elastic wire 21 in this embodiment.

In this embodiment, the stent-graft 100 can be folded and secured easily by adjusting the disposition of the auxiliary elastic wire 5.

This will be described in detail.

As mentioned above, the curved portions (W) of the elastic rings 21 (four portions in this embodiment) are the portions that transform the most during transformation of the ring between the folded and expanded state. Thus, if the transformation of the curved portions (W) is disturbed, a process of folding and expanding the stent-graft 100 is also hindered from being conducted smoothly.

A significant aspect that determines the facility of the stent 100 as a whole to transform between a folded state and an expanded state are the end-parts of the graft 1, which include the outermost elastic rings 21 on both end-parts of the stent-graft 100, and the portion of the graft 1 that is attached to the outermost elastic rings 21. The facility of the stent-graft 100 as a whole to transform is largely related to the facility of the end-parts of the graft 1 to transform.

A concrete explanation follows. The elastic rings 21, with the exception of the outermost elastic rings 21, are sewn to the graft 1 intermittently at only four portions along the diameter of each elastic ring 21. The four portions where each elastic ring 21 is sewn to the graft 1 are at the center of the middle portions (M), which are identical for each ring, and are the portions of the elastic rings 21 that bend the least during transformation. Due to this configuration, when the elastic rings 21 transform, they do so in unison while maintaining the uniform spacing between them, and since the rings are only partially connected to the graft, they can transform independently of the graft, without any significant resistance from the graft.

On the other hand, as mentioned above, the outermost elastic rings 21 arranged at both ends are mounted onto the entirety of the circumference of the graft 1. Thus, as the outermost elastic rings 21 transform, the graft 1 is forced to follow their transformation, which presents a degree of resistance that has an impact on the transformation of the stent-graft 100 as a whole. It is for this reason that the facility of the transformation of both end-parts of the graft 1 largely determines the facility of the transformation of the stent-graft 100 as a whole.

The facility of the transformation of the end-parts of the graft 1 at the curved portion (W), where the transformation is most significant when the graft 1 is transformed to the folded state, strongly affects the facility of the transformation of the entirety of the elastic rings 21. Meanwhile, the middle portions (M) of the elastic rings 21 located at the end-parts of the graft 1 are the portions that transform the least, therefore, the middle portion (M) of the end-part of the graft 1 hardly contributes to the facility of the transformation of the elastic rings 21.

In this embodiment, since the auxiliary elastic wire 5 is arranged so as not to pass at a portion where the graft 1 is forced to transform most significantly while following the transformation of the elastic rings 21, namely at the curved portion (W) of the end-part of the graft 1, the auxiliary elastic wire 5 will hardly hinder the transformation of the elastic rings 21.

As mentioned above, in accordance with the stent-graft 100 of this embodiment, since the shape-maintainability of the end-part of the stent-graft 100 in the expanded state is improved by the auxiliary elastic wire 5, it is possible to prevent an unexpected move of the stent-graft 100 without impairing characteristics of the flexible stent-graft 100 such as a satisfactory flexibility or adhesiveness of the elastic rings 21 to the inner wall of the blood vessel. Consequently, the stent-graft 100 can be used for a long period of time without any conflict.

In addition, since the shape, arrangement, and rigidity of the auxiliary elastic wire 5 are ingeniously set in order to secure the facility of the transformation between the expanded state and the folded state, it is possible to fold the stent-graft 100 and shrink its diameter in the radial direction. This facilitates implanting the stent-graft 100, and expanding it inside of the blood vessel smoothly and securely.

In addition, in accordance with this stent-graft 100, the following effects can be obtained.

Since the auxiliary elastic wire 5 is an endless annular shape without any pointed end, it is unlikely to cause damage to a blood vessel.

Since the graft 1 is made in a bellowed shape and is highly flexible, it is possible for the stent-graft 100 to easily follow the movements (especially expansion and contraction) of the blood vessel and to be securely attached to the inner wall of the blood vessel. As a result of this, it is possible to prevent the stent-graft 100 from moving accidentally from the implanted portion of the blood vessel.

There is a known tendency for portions of a stent-graft implanted in a blood vessel to continuously damage the blood vessel. This tendency is particularly known to occur at high frequency in the area where the blood vessel walls engulf the rear end or downstream portion of a stent-graft. The reasons for this phenomenon are not clearly known. However, upon keen examinations made by the present inventor, it has been found that if the external diameter of the rear end opening of the stent-graft 100 is set to be smaller than the internal diameter of the corresponding blood vessel, it is possible to substantially reduce the likelihood of damage to the blood vessel. This effect is especially noticeable in cases of aortic aneurysm treatment.

In addition, since the front end opening of the stent-graft 100 is mounted on the transporting tube 300 by means of four detachable strings 303, like lines of a parachute, the front end opening of the stent-graft 100 is easily made perpendicular to the axis of the blood vessel, making it possible to securely and appropriately implant the stent-graft 100.

Second Embodiment

Next, a second embodiment of this invention will be explained.

A stent-graft 100 in accordance with this embodiment is arranged to cover the inside the walls of a (distal) aortic arch aneurysm (A).

A concrete explanation will follow.

Figure 13:
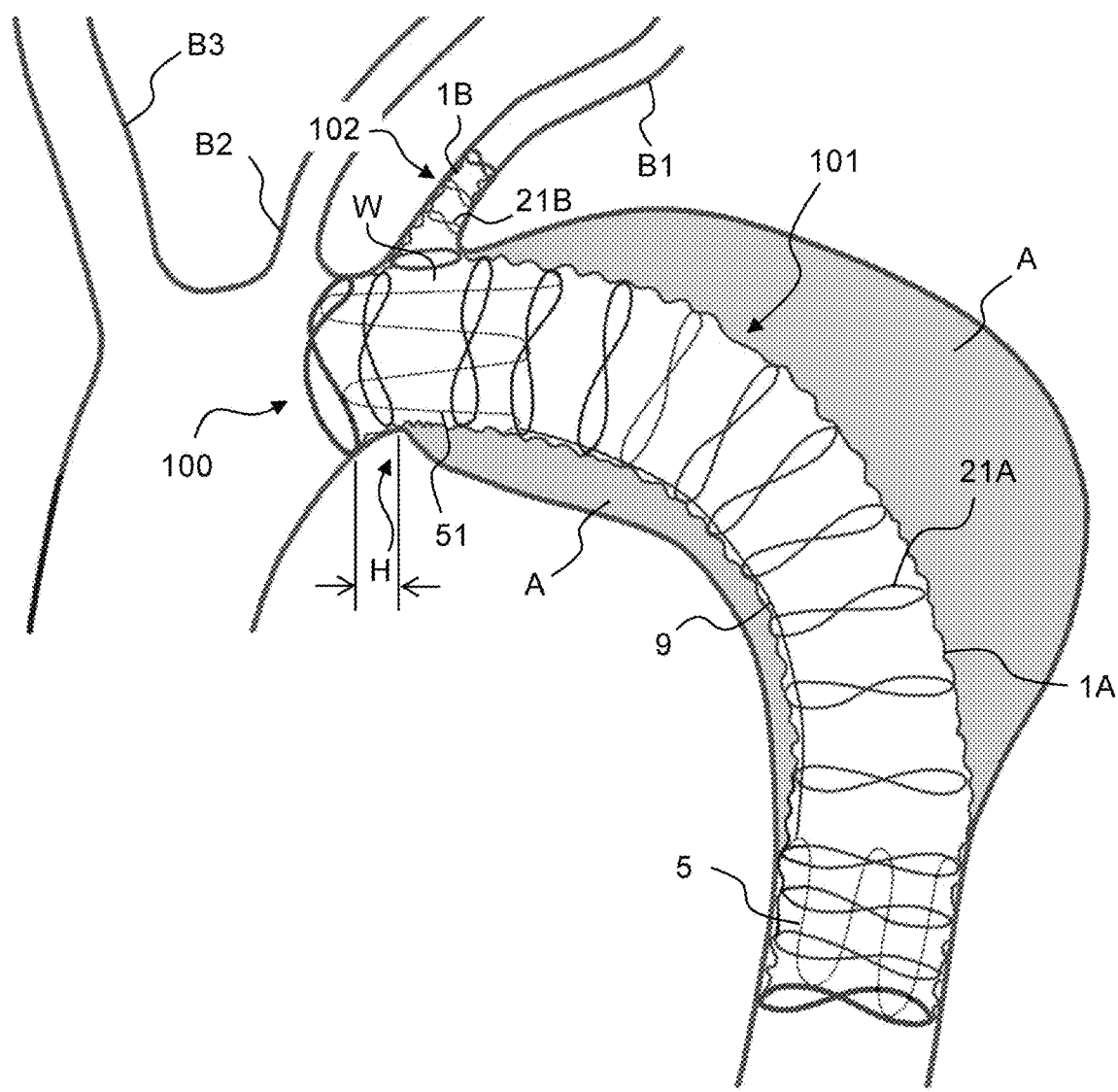
FIG. 13 is a general view showing a state wherein a stent-graft in a second embodiment of this invention is placed in an aortic arch portion.

The stent-graft 100 comprises, as shown in FIG. 13, a main tube 101 that is mounted on an aortic arch portion and covers from the inside the walls of an aortic aneurysm (A), and a diverging tube 102 that diverges from one end-part located in the upstream side of the main tube 101, and that is inserted into a left subclavian artery (B1).

A basic configuration of the main tube 101 is the same as that of the stent-graft, having a single tube, in the first embodiment. More specifically, the main tube 101 comprises a first graft (1A), multiple elastic rings (21A) mounted on the first graft (1A), and auxiliary elastic wires 5, of which one is arranged at the upstream side opening, and the other at the downstream side opening of the first graft (1A).

A resin elastic wire 9 that extends in an axial direction of the tube is arranged on an outer circumferential surface of the main tube 101, on the side opposite the diverging tube 102, so that the main tube 101 is bent along the aortic arch portion in an expanded state due to an elastic restoring force of the resin elastic wire 9.

An upstream opening (end) of the main tube 101 is located between the left subclavian artery (B1) and a left common carotid artery (B2) and extends downstream along the aortic arch portion. A downstream opening (end) of the main tube 101 is located at a downstream side of the aortic aneurysm (A).

The diverging tube 102 is comprised of a second graft (1B) and multiple second elastic rings (21B) mounted on the second graft (1B). No auxiliary elastic wire is provided at a distal end-part of the diverging tube 102.

A proximal end of the diverging tube 102 is mounted between the wide-spaced first wire elements 51 of the auxiliary elastic wire 5 arranged at the upstream side end-part of the main tube 101, namely at the curved portion (W). The curved portion (W) where the diverging tube 102 is mounted is a portion that when bent does not protrude toward the adjacent distal end side of the stent-graft, but rather bends away from the distal end side, or toward the center of the stent-graft.

The reason for the above described configuration will be explained from here on. As mentioned above, when the stent-graft 100 is implanted in the aortic arch portion, the opening end of the main tube 101 is in a state of being slightly bent. In this state, the curved portion (W) is also slightly bent due to its tendency to bend along with the body of the stent-graft, such as when the stent-graft 100 is transformed to a folded state. More concretely, from among the four curved portions (W), a pair of curved portions (W) that are non-adjacent and face each other bend so as to protrude toward the distal end side of the stent-graft, and the other pair (the remaining pair) of curved portions (W) bend in the opposite direction, or toward the center of the stent-graft.

When the stent-graft 100 is implanted in an aortic arch portion, the curved portion (W) on which the diverging tube 102 is mounted is positioned along the section of the inner wall of the aortic arch portion that has the smallest degree of curvature. Accordingly, the paired non-adjacent curved portion (W) that faces the curved portion (W) on which the divergent tube 102 is mounted is positioned along the section of the inner wall of the aortic arch portion that has the greatest degree of curvature.

Thus, if the diverging tube 102 is mounted on a curved portion (W) that bends so as to protrude toward the distal end side of the stent-graft, a protrusion of the curved portion (W) is positioned against the inner wall of the aortic arch portion that has the least degree of curvature. In this position there exists a possibility that the protrusion will fail to follow the curve of the inner wall of the aortic arch portion, resulting in movement of the stent graft 100 that could cause the diverging tube 102 to turn away from the inner wall of the aortic arch portion arc with the least degree of curvature. In order to minimize as much as possible the potential for this to occur, the diverging tube 102 is mounted on the above-mentioned curved portion (W).

In accordance with this embodiment, the effect of the auxiliary elastic wire 5 becomes especially noticeable.

The significance of the elastic wire 5 in this embodiment is explained from here on.

In the case of a distal aortic arch aneurysm (A), since the left subclavian artery (B1), the left common carotid artery (B2), and a right brachiocephalic artery (B3) diverge successively from the upstream portion of the distal aortic arch aneurysm (A), it is not possible to extend the main tube 101 that covers the aortic arch aneurysm (A) to the upstream side, since such an extension would obstruct the openings to B2 and B3. In addition, the aortic arch portion is strongly curved. Therefore, it is necessary to arrange the end-part of the main tube 101 between the openings to B1 and B2 along the blood vessel at a portion (H), which is a portion of the blood vessel that is strongly curved.

If a conventional 'soft' stent-graft is arranged at the strongly curved portion (H), it is more likely that the opening part of the stent-graft will become tilted so as to be diagonally inclined relative to the axial direction of the blood vessel. As a result of this, the blood might leak from the tilted opening part, and the stent-graft might move out of position. Alternatively, if a 'hard' stent-graft is arranged, it is difficult for the 'hard' stent-graft to fit into the strongly curved portion (H). Accordingly, in the case of an aneurysm or a dissociative aortic aneurysm, under certain circumstances, it may be extremely difficult to implant the stent-graft via the catheter.

However, since the stent-graft 100 of this embodiment is 'soft,' it is possible for the stent-graft 100 to fit into the blood vessel at the strongly curved portion (H) and to securely prevent the opening from being tilted, due to the influence of the auxiliary elastic wire 5.

In addition, in this embodiment, since the diverging tube 102, which diverges from the main tube 101, enters the left subclavian artery (B1), and functions as a so-called positioning member, it is possible to securely fit the stent-graft 100 to the blood vessel if the stent-graft 100 is tailored to a shape corresponding to the shape of the blood vessel of a patient.

Due to the above-mentioned reasons, in accordance with the stent-graft 100 in accordance with this embodiment, a remarkable effect can be expected, wherein the stent-graft 100 can be implanted via a catheter without the need for a thoracotomy, even in the case of an aortic arch aneurysm (A).

The present claimed invention encompasses a multitude of relevant embodiments and is not limited to the embodiments described in detail above.

For example, in certain embodiments, the auxiliary elastic wire may be mounted on the rear end opening part of the stent-graft. In the second embodiment, the auxiliary elastic wire may be mounted also on the end-part of the diverging tube.

Figure 14:
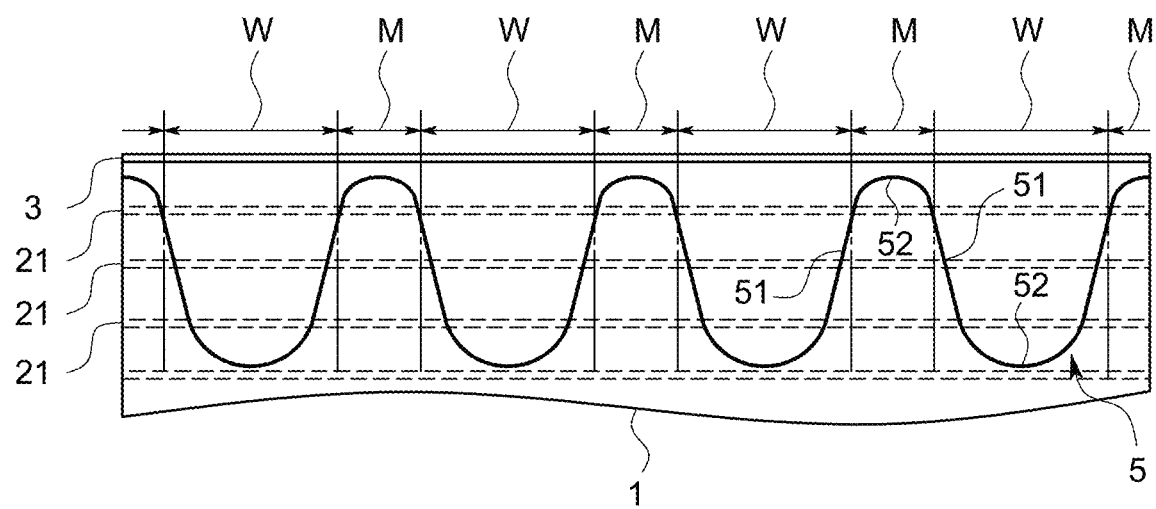
FIG. 14 is a plane expansion view of a stent-graft to explain an auxiliary elastic wire in another embodiment of this invention.
Figure 15:
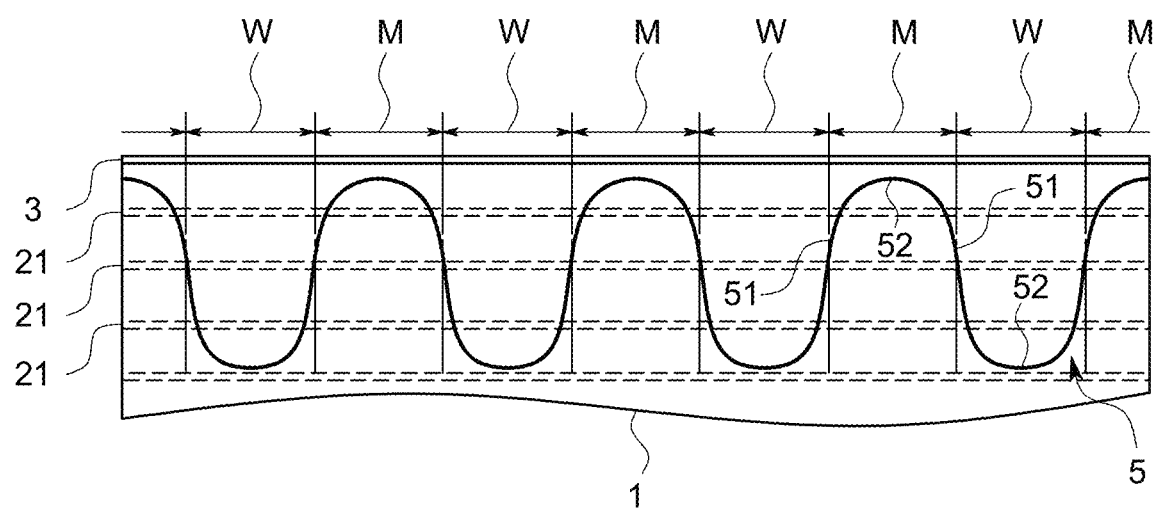
FIG. 15 is a plane expansion view of a stent-graft to explain an auxiliary elastic wire in a further different embodiment of this invention.

The shape of the auxiliary elastic wire 5 is not necessarily a shape where the first wire element 51 is completely parallel to the axis of the tubular; it may also be slightly inclined as shown in FIG. 14. In addition, as shown in FIG. 15, the shape of the first wire element 51 is not limited to a straight line, but may be a slightly curved line as well.

In addition, a portion of the adjacent first wire elements 51 whose width is narrow may be arranged to correspond to the curved portion, or the first wire elements 51 may be arranged at the same intervals in the circumferential direction.

The auxiliary elastic wire is sewn to the graft in the above-mentioned embodiments; however, the auxiliary elastic wire may be directly mounted on the elastic ring without being mounted on the graft.

Figure 16:
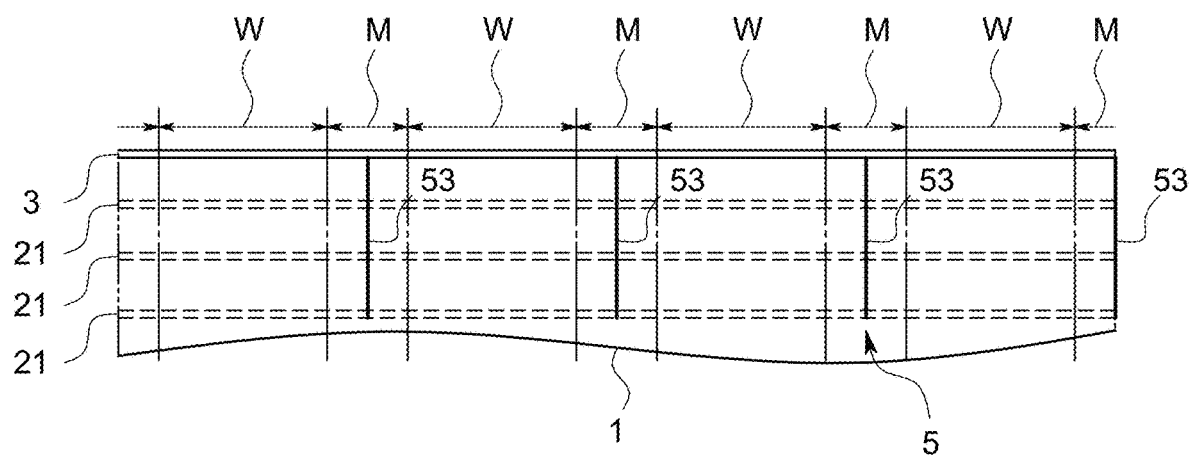
FIG. 16 is a plane expansion view of a stent-graft to explain an auxiliary elastic wire in a further different embodiment of this invention.

Furthermore, the auxiliary elastic wire 5 is not limited to an endless annular shape. For example, as shown in FIG. 16, the auxiliary elastic wire 5 may be discontinuous, comprising multiple wire elements 53, each of which is linear or slightly curved, extending parallel to the axis of the tubular shape. In this case, it is preferable that the elastic wire elements 53 are arranged at a position that avoids the strongly curved portion (W), and in which case, there are four wire elements 53.

In the above-mentioned embodiments, the auxiliary elastic wire 5 is mounted on the outer circumferential surface of the graft 1; however, the auxiliary elastic wire 5 may also be mounted on an inner circumferential surface of the graft 1.

The stent may be helical.

A detachable member that is the same as the member that is arranged for the front end opening edge of the stent-graft may be arranged also on the rear end opening edge of the stent-graft. In this case, a second transporting tube to engage the pulling string (a second pulling string) may pass through the catheter 200, and the second pulling string may be hooked to a second engaging wire that passes inside of the second transporting tube for which a window is provided.

Figure 17:
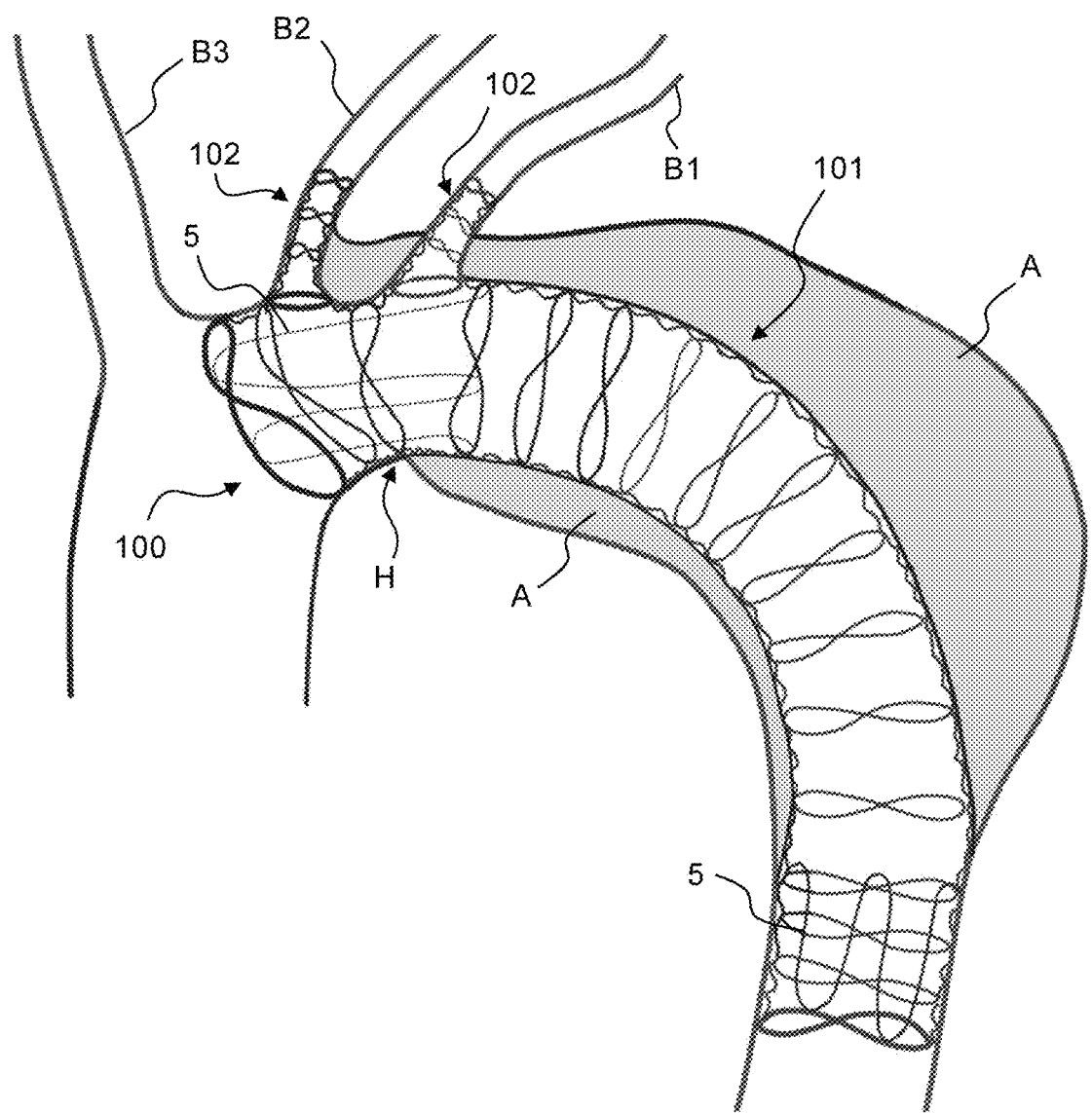
FIG. 17 is a general view showing a state wherein a stent-graft in a further different embodiment of this invention is placed in an aortic arch portion.

In the above-mentioned second embodiment, the stent-graft having one diverging tube that is inserted into the left subclavian artery is used. However, in the case that an aneurysm extends to the left common carotid artery or to the right brachiocephalic artery, for example, the stent-graft may have two or three diverging tubes. FIG. 17 shows the stent-graft 100 having two diverging tubes.

In addition, in the second embodiment, the diverging tube extends from the upstream side end-part of the main tube; however, in the case that an aneurysm is in the aorta ascendens (ascending aorta), it is preferable that the diverging tube extend from the downstream side end-part of the main tube.

In the above-mentioned case, since the upstream end-part or the downstream end-part of the main tube is positioned in the aortic arch portion where the curvature is strong, the auxiliary elastic wire arranged at the end-part functions sufficiently so that the same effects can be produced.

In addition, it is a matter of course that the present claimed invention may be modified in various ways without departing from the spirit of the invention.

EXPLANATION OF REFERENCE CHARACTERS

100 . . . stent-graft
1 . . . graft
2 . . . stent
21 . . . elastic ring
5 . . . auxiliary elastic wire
51 . . . first wire element
52 . . . second wire element
200 . . . catheter (delivery sheath)

The invention claimed is:

1. A stent-graft comprising a graft of a tubular shape and at least one elastic ring at least at one end-part of the graft, and configured to be housed into a delivery sheath, with the at least one elastic ring being transformed into a saddle-shape, and the graft being folded in accordance with the transformation of the at least one elastic ring, wherein
an auxiliary elastic wire, whose rigidity is lower than that of the at least one elastic ring, is furthermore provided only at one or both end-parts of the graft, and the auxiliary elastic wire is connected to the graft or to the at least one elastic ring, and
the auxiliary elastic wire surrounds the graft in a circumferential direction, a concave portion and a convex portion of the auxiliary elastic wire repeated in the circumferential direction in an expanded state in which the at least one elastic ring is in a fully expanded state having a maximum diameter achieved by an elastic restoring force of the at least one elastic ring, wherein
a number of concave portions and convex portions of the auxiliary elastic wire is larger than a number of concave portions and convex portions of the at least one elastic ring in a folded state of the stent-graft in which the at least one elastic ring is folded to have a shrunken diameter as compared to the maximum diameter.

2. The stent-graft described in claim 1, wherein
the auxiliary elastic wire comprises multiple first wire elements intermittently arranged in the circumferential direction of the graft, and each of the first wire elements is connected to the at least one elastic ring arranged at the at least one end-part of the graft in a condition of intersecting with the at least one elastic ring.

3. The stent-graft described in claim 2, wherein
the auxiliary elastic wire is a continuous annular shape that surrounds the graft in the circumferential direction, the concave portion and the convex portion of the auxiliary elastic wire repeated in the circumferential direction, and the auxiliary elastic wire comprises multiple second wire elements, each of which forms the concave portions and the convex portions, and the multiple first wire elements, each of which links the concave portion and the convex portion.

4. The stent-graft described in claim 1, wherein
the auxiliary elastic wire is arranged at a position avoiding both a top of a convex portion of the at least one elastic ring arranged at the at least one end-part of the graft and a vicinity of the top thereof.

5. The stent-graft described in claim 3, wherein
eight pieces of the first wire elements and eight pieces of the second wire elements are provided respectively.

6. The stent-graft described in claim 5, wherein
a top of a convex portion of an outermost elastic ring at the one or both end-parts of the graft is located between adjacent convex parts of the auxiliary elastic wire.

7. The stent-graft described in claim 6, wherein
a length in the circumferential direction of the second wire element that forms the concave portion is longer than a length in the circumferential direction of the second wire element that forms the convex portion.

8. The stent-graft described in claim 3, wherein
the first wire elements extend in an axial direction, and the second wire elements are connected to the adjacent first wire elements while curving smoothly between the first wire elements.

9. The stent-graft described in claim 1, wherein
an opening diameter of the stent-graft arranged in a downstream side of a blood vessel is smaller than a diameter of a middle part of the stent-graft.

10. The stent-graft described in claim 1, wherein
the stent-graft is configured to be mountable on an aortic arch portion so as to cover an aortic aneurysm from the inside and further comprises a diverging tube that diverges from the graft and that is insertable into a blood vessel that diverges from the aortic arch portion.

11. A stent-graft comprising a graft of a tubular shape and an elastic and helical coil arranged to span across both end-parts of the graft, and configured to be housed in a delivery sheath, where the elastic and helical coil transforms into a saddle shape and the graft is folded in accordance with the transformation of the elastic and helical coil, wherein
an auxiliary elastic wire whose rigidity is lower than that of the elastic and helical coil is furthermore provided only at one or both end-parts of the graft, and the auxiliary elastic wire is connected to the graft or to the elastic and helical coil at the one or both end-parts throughout multiple pitches, and the auxiliary elastic wire surrounds the graft in a circumferential direction, a concave portion and a convex portion of the auxiliary elastic wire repeated in the circumferential direction, the repeated concave portions and the repeated convex portions extending in an axial direction to cross a second-to-end elastic ring.

12. A stent-graft comprising a graft of a tubular shape and at least one elastic ring arranged at one end-part of the graft, and configured to be housed into a delivery sheath, the stent-graft configured to transform between an expanded state, in which the at least one elastic ring is in a fully expanded state having a maximum diameter achieved by an elastic restoring force of the at least one elastic ring, and a folded state in which the at least one elastic ring is folded to have a shrunken diameter as compared to the maximum diameter, with the at least one elastic ring being transformed into a saddle-shape in the folded state, and the graft being folded in the folded state in accordance with the transformation of the at least one elastic ring, wherein an auxiliary elastic wire, whose rigidity is lower than that of the at least one elastic ring, is furthermore provided only at one or both end-parts of the graft, and the auxiliary elastic wire is connected to the graft or to the at least one elastic ring, and the auxiliary elastic wire surrounds the graft in a circumferential direction, a concave portion and a convex portion of the auxiliary elastic wire repeated in the circumferential direction in the expanded state, the repeated concave portions and the repeated convex portions extending in an axial direction to cross a second-to-end elastic ring in the expanded state.

13. The stent-graft described in claim 12, wherein a length of the auxiliary elastic wire is longer than a length of the at least one elastic ring, such that the concave portion and the convex portion of the auxiliary elastic wire are repeated in the circumferential direction in the expanded state in which the at least one elastic ring is in the fully expanded state having the maximum diameter achieved by the elastic restoring force of the at least one elastic ring.

14. The stent-graft described in claim 1, wherein a length of the auxiliary elastic wire is longer than a length of the at least one elastic ring, such that the number of concave portions and convex portions of the auxiliary elastic wire is larger than the number of concave portions and convex portions of the at least one elastic ring in the folded state of the stent-graft in which the at least one elastic ring is folded to have the shrunken diameter as compared to the maximum diameter.

* * * * *